United States Patent [19]
Saito et al.

[11] Patent Number: 6,037,501
[45] Date of Patent: Mar. 14, 2000

[54] PROCESS FOR PRODUCING FLUORENE OR ITS DERIVATIVES

[75] Inventors: Noboru Saito; Toshiya Iida; Isamu Maeda, all of Osaka, Japan

[73] Assignee: Nippon Shokubai Co., Ltd., Osaka, Japan

[21] Appl. No.: 09/068,609

[22] PCT Filed: Nov. 5, 1996

[86] PCT No.: PCT/JP96/03232

§ 371 Date: May 6, 1988

§ 102(e) Date: May 6, 1998

[87] PCT Pub. No.: WO97/17311

PCT Pub. Date: May 15, 1997

[30] Foreign Application Priority Data

Nov. 7, 1995 [JP] Japan .................................. 7-288545

[51] Int. Cl.[7] .......................... C07C 45/00; C07C 49/00; C07C 45/87; C07C 49/76; B01J 31/00
[52] U.S. Cl. .......................... 568/300; 568/303; 568/308; 568/309; 568/320; 502/102; 502/103
[58] Field of Search .................................. 568/300, 303, 568/308, 309, 320; 502/102, 103

[56] References Cited

U.S. PATENT DOCUMENTS

| | | | |
|---|---|---|---|
| 1,374,695 | 4/1921 | Weiss et al. ............................... | 568/321 |
| 1,892,768 | 1/1933 | Jaeger ...................................... | 568/321 |
| 2,956,065 | 10/1960 | DeWalt, Jr. et al. ..................... | 502/218 |
| 3,325,551 | 6/1967 | Suld ......................................... | 585/411 |
| 3,755,198 | 8/1973 | Stratenus .................................. | 252/466 |
| 4,038,175 | 7/1977 | Bhasin ..................................... | 252/466 |
| 4,299,987 | 11/1981 | Dolhyj et al. ............................ | 568/321 |

FOREIGN PATENT DOCUMENTS

| | | |
|---|---|---|
| 1262268 | 3/1968 | Germany . |
| 1940051 | 5/1979 | Germany . |
| 59-216846 | 12/1984 | Japan . |
| 60-233028 | 11/1985 | Japan . |
| 61-78747 | 4/1986 | Japan . |

OTHER PUBLICATIONS

B. Akermark et al.: "Palladium–promoted cyclization of diphenyl ether, diphenylamine and related compounds" J. Org. Chem., vol. 40, No. 9, 1975, pp. 1365–1367, XP002086435 * p. 1365; examples 1C, 2C.

P. Hanson et al.: "Sandmeyer reactions" J. Chem. Soc. Perkin Trans. 2, (1994) vol. 4, pp. 691–696 XP002086436 see p. 691, Scheme 1.

Patent Abstracts of Japan vol. 10, No. 103 (C–340), Apr. 18, 1986, abstracting JP 60 233028A (Nippon Shokubai Kagaku Kogyo), Nov. 19, 1985.

Patent Abstracts of Japan vol. 10, No. 252 (C–369), Aug. 29, 1986, abstracting JP 61 078747 A (Nippon Shokubai Kagaku Kogyo), Apr. 22, 1986.

J. Chem. Soc. Perkin Trans., vol. I, 11, 1236–1241 (1976).

zh. Pyirl Khim 35, 693–696 (1962).

Kogyo Kagaku Zasshi, 56(6), 413–416 (1953).

*Primary Examiner*—Gary L. Kunz
*Assistant Examiner*—Everett White
*Attorney, Agent, or Firm*—Sughrue, Mion, Zinn, MacPeak & Seas, PLLC

[57] ABSTRACT

By subjecting an aromatic compound of the formula (I), which is an inexpensive raw material, to a vapor-phase intramolecular cyclodehydrogenation reaction, fluorenes of the formula (II) can be obtained industrially advantageously in a high yield. Fluorenes (II) are expected to be used as raw materials for heat-resistant epoxy resins, polycarbonates or polyesters.

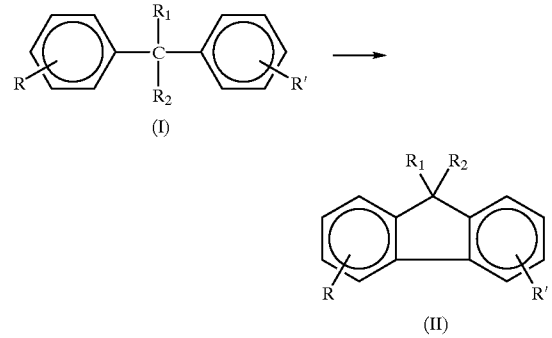

wherein $R_1$ and $R_2$ each represent a hydrogen atom, a methyl group or an ethyl group, or $R_1$ and $R_2$ represent =O at the same time; and R and R' each represent a hydrogen atom, an alkyl group having 1 to 4 carbon atoms or an alkoxy group having 1 to 4 carbon atoms.

6 Claims, No Drawings

PROCESS FOR PRODUCING FLUORENE OR ITS DERIVATIVES

This application is a 371 of PCT/JP96/03232 filed Nov. 5, 1996.

TECHNICAL FIELD

The present invention relates to a process for the preparation of fluorenes, a process for the preparation of fluorenones from inexpensive and easily available diphenylmethanes using the process, and a catalyst for use in such processes. Fluorenones are useful as intermediates for organic synthesis and raw materials for resins. Particularly, bisphenol derivatives are useful as raw materials for heat-resistant epoxy resins, polycarbonates or polyesters.

BACKGROUND ART

Fluorenones are compounds of high utility as intermediates for organic synthesis or raw materials for resins. Known examples of the preparation process of fluorenones include oxidation of fluorenes and liquid phase oxidation of benzophenone using palladium acetate as an oxidizing reagent.

As the process for the oxidation of fluorenes, liquid phase reaction is disclosed in German Offenlegungsschrift DE-1, 262,268 and 1,940,051, while vapor phase reaction is disclosed in JP-A-60-233028 (the term "JP-A" as used herein means an "unexamined published Japanese patent application").

The raw material fluorenes are however mainly obtained by separation from tar. From the viewpoints of the separation cost and problem of limited resources, use of the tar is not economically advantageous.

Concerning a process for obtaining fluorenes by synthesis, catalytic cyclodehydrogenation of an alkylbiphenyl compound is described in U.S. Pat. No. 3,325,551. According to its description, 9,9-dimethylfluorene is prepared from 2-isopropylbiphenyl as shown specifically by the following reaction formula:

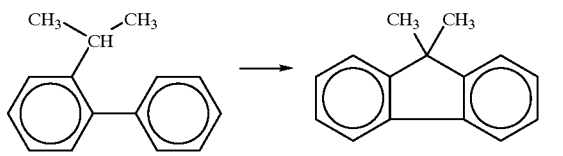

The above process is however economically disadvantageous because the raw material biphenyl compound should be separated from a tar fraction similar to the case of fluorenes or a coupling reaction of benzene at high temperature is required where obtaining by synthesis. In addition, the raw material alkylbiphenyl compound requires introduction of an alkyl group into a specific position of a benzene ring, so that such a compound is not an easily available compound.

On the other hand, processes for the synthesis of a fluorenone from benzophenone are disclosed in J. Org. Chem. Vol. 40, No. 9, 1365–1367(1975); J. Chem. Soc. Perkin Trans Vol.I. 11, 1236-(1976); and the like.

The above processes are however accompanied with the industrial problems such as necessity of a large amount of palladium, low productivity per expensive palladium, long reaction time and insufficient yield, because the reaction effected in these processes is a reagent reaction in which palladium acetate is added to benzophenone in at least an equivalent amount, and is also a liquid phase reaction.

Accordingly, in view of the above circumstances, an object of the present invention is to provide an industrially advantageous process for the preparation of fluorenes at a low cost and in a high yield.

DISCLOSURE OF THE INVENTION

The present inventors have made an investigation to solve the above-described problems. As a result, it has been found that by a catalytic dehydrogenation reaction in an industrially desirable vapor phase, fluorenes can be obtained in a high yield from a diphenylmethane-base aromatic compound which is easily available inexpensively.

The present invention therefore provides a process for the preparation of fluorenes represented by the following formula (II):

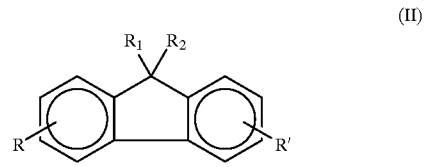

wherein $R_1$ and $R_2$ each represent a hydrogen atom, a methyl group or an ethyl group, or $R_1$ and $R_2$ together represent =O, and R and R' each represent a hydrogen atom, an alkyl group having 1 to 4 carbon atoms or an alkoxy group having 1 to 4 carbon atoms, which comprises subjecting an aromatic compound represented by the following formula (I):

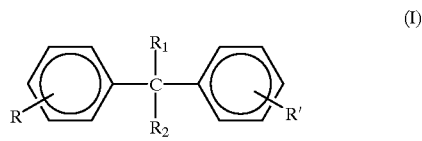

wherein $R_1$, $R_2$, R and R' are the same as defined in (II) above to a vapor-phase intramolecular cyclodehydrogenation reaction.

Described specifically, it has been found that according to the above process of the present invention, two aromatic rings in the formula (I) form a ring by the intramolecular dehydrogenation reaction in a vapor phase, whereby fluorenes are prepared in a good yield. By using the present invention, fluorenes can be prepared conveniently in a high yield without using biphenyls but using an easily-available aromatic compound of the formula (I) as a starting material.

There has also been found in the present invention a process for synthesizing fluorenones easily in a good yield through fluorenes or benzophenones using diphenylmethanes as a starting material which can be prepared easily from inexpensive raw materials.

Described specifically, the above process is a process for the preparation of fluorenones represented by the following formula (V):

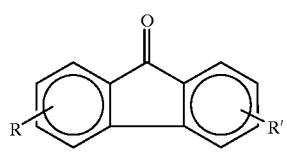
(V)

wherein R and R' each represent a hydrogen atom, an alkyl group having 1 to 4 carbon atoms or an alkoxy group having 1 to 4 carbon atoms, which comprises subjecting diphenylmethanes represented by the following formula (III):

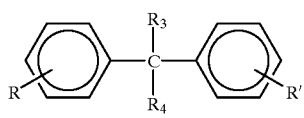
(III)

wherein $R_3$ and $R_4$ each represent a hydrogen atom, a methyl group or an ethyl group and R and R' are the same as defined above, to a vapor-phase intramolecular cyclodehydrogenation reaction, thereby preparing corresponding fluorenes represented by the following formula (IV):

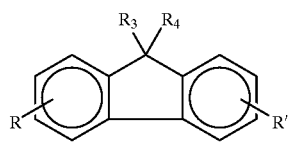
(IV)

wherein $R_3$, $R_4$, R and R' are the same as defined above, and then subjecting the resulting fluorenes to a vapor-phase oxidation reaction; or a process for the preparation of fluorenones represented by the above formula (III), which comprises subjecting diphenylmethanes represented by the above formula (III) to a vapor-phase oxidation reaction, thereby preparing benzophenones represented by the following formula (VI):

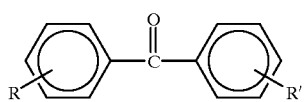
(VI)

wherein R and R' are the same as defined above, and then subjecting the resulting benzophenones to a vapor-phase intramolecular cyclodehydrogenation reaction.

BEST MODES FOR CARRYING OUT THE INVENTION

The vapor-phase intramolecular cyclodehydrogenation reaction of an aromatic compound of the formula (I) according to the present invention is preferably conducted in the presence of a catalyst. The catalyst for use in the vapor-phase intramolecular cyclodehydrogenation reaction of the aromatic compound of the formula (I), which can be used, is catalysts generally used as a dehydrogenation catalyst. Examples thereof include noble metal catalysts, metal catalysts, and oxide catalysts. Particularly, noble metal catalysts are preferred because of high conversion rate and high selectivity.

Specific examples of the noble metal catalyst include Pt, Pd, Ru and Rh. Of these, Pt is preferred, with Pt supported on a carrier being particularly preferred. Examples of the carrier for the above noble metal catalysts include activated carbon, $SiO_2$, $Al_2O_3$, $TiO_2$ and $ZrO_2$.

Examples of the metal catalyst include metals such as Cu or Ni, and these metals supported on ZnO, $Al_2O_3$, $Cr_2O_3$, $SiO_2$ or the like.

Preferred examples of the oxide catalyst include those containing ZnO, $ZrO_2$, an alkaline earth metal oxide, $Cr_2O_3$, $CeO_2$, $Al_2O_3$ or the like.

The reaction method used is, for example, a fixed bed, a fluidized bed or a moving bed. The reaction may be conducted continuously although varying depending on the catalyst used. It is also possible to conduct the reaction under activation in order to remove coking during the reaction.

As the reaction conditions, after the aromatic compound represented by the above formula (I) is vaporized in a conventional manner, it may be used either in the form of the raw material or in the diluted form with an inert gas such as nitrogen. The reaction can be conducted either under normal pressure or under reduced pressure.

The space velocity (SV) of raw material gas is preferably 10 to 1,000 $hr^{-1}$ based on the aromatic compound of the formula (I) used as the raw material. So, when the aromatic compound of the formula (I) is diluted with nitrogen to 10 mole %, the space velocity is preferably 100 to 10,000 $hr^{-1}$.

No limitation is imposed on the reaction temperature so long as it is at least a temperature allowing the raw material and the product to maintain the vapor phase condition. Preferred is 200 to 700° C., with 250 to 550° C. being particularly preferred.

The present invention also provides a process for the preparation of fluorenones represented by the formula (V) from diphenylmethanes represented by the formula (III) through the below-described two routes using two techniques of oxidation reaction and cyclohydrogenation reaction in combination. The process makes it possible to prepare, in a high yield, fluorenes of the formula (V) having industrially high utility from a diphenylmethane of the formula (III) which is an easily available raw material.

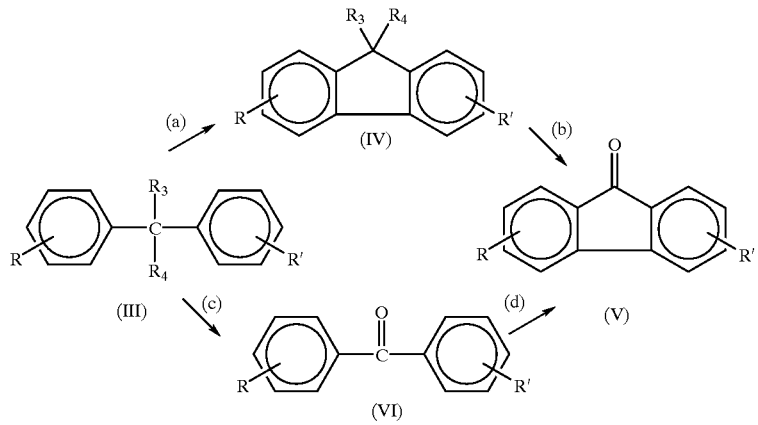

In the above reaction routes, each of the reaction (a) and the reaction (d) is a vapor-phase intramolecular cyclodehydrogenation reaction.

Examples of the diphenylmethanes represented by the formula (III) include diphenylmethane, 1,1-diphenylethane and 2,2-diphenylpropane. One or two benzene rings may have an alkyl group or an alkoxy group, each having 1 to 4 carbon atoms, and preferably 1 to 2 carbon atoms, as a substituent. Of these, 1,1-diphenylethane is preferred because it is easily available as a tar fraction, an FCC fraction, a by-product of styrene or the like. According to the present invention, an objective product can be obtained in a high yield even when a diphenylethane fraction of low purity is used.

For the synthesis (reaction (b)) of the fluorenones of the formula (V) from the fluorenes of the formula (IV) or for the synthesis (reaction (c)) of the benzophenones of the formula (VI) from the diphenylmethanes of the formula (III), the use of liquid phase oxidation is known but the use of catalytic vapor-phase oxidation is industrially preferred. By using the catalytic vapor-phase oxidation, preparation steps from the diphenylmethanes of the formula (III) to the fluorenones of the formula (V) can all be carried out through the reaction in a vapor phase. The fluorenones of the formula (V) can therefore be obtained in a high yield without isolation and purification of the fluorenes of the formula (IV) or benzophenones of the formula (VI) as an intermediate.

Examples of the catalytic vapor-phase oxidation method usable in the above reaction (b) include the methods described in, for example, U.S. Pat. No. 1,374,695, Zh. Pyirl Khim, 35, 693–696(1962), Kogyo Kagaku Zasshi, 56(6), 413–416(1953), U.S. Pat. No. 1,892,768, U.S. Pat. No. 2,956,065 and JP-A-60-233028.

Examples of the catalytic vapor-phase oxidation method usable in the reaction (c) include the methods described in, for example, JP-A-59-216846, JP-A-61-78747 and U.S. Pat. No. 4,299,987.

EXAMPLES

The present invention is described in more detail below by the Examples.

EXAMPLES 1 and 2
(Reaction (a))
(Preparation of Catalyst)

Shirasagi WHc activated carbon as a carrier was subjected to vacuum impregnation with an aqueous $H_2PtCl_6$ solution, followed by hydrogen reduction (500° C.×6 Hrs), to obtain a catalyst supported Pt in an amount of 5 wt %.

(Reaction)

A 10 mm diameter SUS tube was filled with 10 g of the catalyst thus obtained (9–20 mesh). A gas of diphenylmethanes was diluted with $N_2$ to a concentration of 10 vol %. The reaction tube was maintained at a temperature of 500° C. and the reaction was conducted at SV of 1000 $h^{-1}$ (in terms of STP). The results of the reaction are shown below in Table 1.

TABLE 1

| Example | Catalyst | Raw material | (Reaction conditions) SV | Temp. | (Results of reaction) Conversion | Selectivity |
|---|---|---|---|---|---|---|
| 1 | 5 wt % Pt/activated carbon | diphenyl-methane | 1000 $hr^{-1}$ | 450° C. | 44.3% | 95.6% |
| 2 | 5 wt % Pt/activated carbon | 1,1-diphenyl-ethane | 1000 $hr^{-1}$ | 450° C. | 41.5% | 87.4% |

In Table-1, the conversion (conversion of the raw material diphenylmethanes) and selectivity (selectivity to the fluorenes) were calculated in accordance with the following equations, respectively (hereinafter the same).

$$\text{Conversion (\%)} = \frac{\text{(Moles of the raw material supplied)} - \text{(Moles of the unreacted raw material)}}{\text{(Moles of the raw material supplied)}} \times 100$$

$$\text{Selectivity (\%)} = \frac{\text{(Moles of the fluorenes formed)}}{\text{(Moles of the raw material supplied)} - \text{(Moles of the unreacted raw material)}} \times 100$$

EXAMPLE 3
(Reaction (b))

From the fluorene obtained in Example 1, the raw material diphenylmethane was separated by the conventional distillation operation. The fluorene was subjected to a vapor-phase oxidation reaction in the same manner as the method described in JP-A-60-233023 as follows.

(Preparation of Catalyst)

3.36 g of ammonium metavanadate were added to 200 cc of water, and 6.7 g of oxalic acid were added thereto to dissolve the same therein. 0.84 g of cesium sulfate and 0.60 g of potassium sulfate were added to the resulting vanadate solution to form a uniform solution. 30 g of titanium dioxide (lutile type BET surface area: 6 m²/g) were added to the resulting solution, followed by thoroughly mixing with a homomixer to prepare a catalyst slurry.

The above catalyst slurry liquid was sprayed and baked on 100 cc of a spherical silicon carbide carrier having an average diameter of 3 mm which rotated under heating to 150–250° C., followed by calcination at 520° C. for 6 hours under an air flow, thereby obtaining a final catalyst. The catalyst thus obtained contained $V_2O_5$, $TiO_2$, $Cs_2O$ and $K_2O$ at a weight ratio of 8:92:2:1. The amount of the active substance supported on the carrier was 11.5 g/100 cc carrier.

(Oxidation Reaction)

A stainless-made reaction tube having an inner diameter of 25 mm was filled with 80 cc of the catalyst obtained above and the tube wall temperature was set at 385° C. Air was then introduced into a solution obtained by dissolving a 98.4 wt % purity fluorene under heat. After the air had a fixed fluorene concentration, it was introduced into the catalyst layer. The fluorene at that time had a gas concentration of 33.3 g/Nm³ and air velocity was 1500 hr⁻¹ (STP).

The total amount of the fluorenone in the gas in the outlet of the reactor, unreacted raw material, and by-products such as phthalic acid and maleic acid was collected by cooling. After dissolving in acetone, it was subjected to analysis by gas chromatography. The uncondensed contents such as CO and $CO_2$ were also analyzed by gas chromatography. As a result, it showed the conversion of 99.0% and the selectivity of 89.7%.

Incidentally, the crude fluorenone collected by cooling contained 2.1 wt % of phthalic anhydride and 0.1 wt % of maleic anhydride.

Even after the reaction was continued for 2,000 hours, no change was observed in the reaction results.

EXAMPLE 4

(Reaction (b))

A vapor-phase oxidation reaction was conducted using the same catalyst as obtained in Example 3 and under the same reaction conditions as in Example 3 except that fluorene was replaced by 9-methylfluorene obtained in Example 2. As a result, the conversion of 9-methylfluorene was 99.5% and the selectivity to a fluorenone was 81.0%.

EXAMPLE 5

(Reaction (c))

A diphenylmethane was subjected to a vapor-phase oxidation reaction in the same manner as in the method described in JP-A-59-216846 as follows, thereby obtaining a benzophenone.

(Preparation of Catalyst)

A uniform aqueous solution containing 10 moles of lead nitrate and 10 moles of titanyl nitrate was added under stirring to an aqueous solution containing 22 moles of oxalic acid, which solution had been maintained at 80° C., thereby obtaining a suspension of titanyl lead oxalate. Water was removed from the resulting suspension by filtration and drying, followed by calcination at 800° C., thereby obtaining lead titanate in the form of powder. 36.3 g of the above-obtained lead titanate powder and 9.2 g of silicon carbide whisker (having a fiber diameter ranging from 0.05 to 0.6 μm with 0.2 μm on average and a fiber length ranging from 5 to 50 μm with 20 μm on average) were added to 200 ml of water having 20 g of ammonium nitrate dissolved therein to suspend those in water. The resulting suspension was sprayed on silicon carbide carriers having an average diameter of 3 mm which rotated under heating in the range of 150 to 400° C., thereby obtaining a lead titanate supported catalyst. The composition of the catalyst thus obtained was, as PbO and $TiO_2$, PbO:$TiO_2$=73.6:26.4 (weight ratio). The whisker was contained in an amount of 20 wt % based on the weight of the composition carried.

(Oxidation Reaction)

A tubular reactor having an internal diameter of 21 mm was filled with 90 g of the catalyst obtained above and the tube wall temperature was set at 390° C. A mixture of 1.9 g of a diphenylmethane and 120 liters of air was then introduced into the reaction tube at a space velocity (SV) of 1,500 hr⁻¹ (STP). At that time, the raw material gas concentration was 0.4 mole %.

The total amount of the unreacted raw materials and condensable products discharged from the reaction tube was collected by cooling and then dissolved in a solvent. Each component was analyzed with gas chromatography. As a result, the conversion was 98.1% and the benzophenone selectivity was 92.8%.

EXAMPLES 6 and 7

(Reaction (c))

1,1-Diphenylethane was subjected to a vapor-phase oxidation reaction in the same manner as in the method described in JP-B-61-78747 as follows, thereby obtaining benzophenone.

(Preparation of Catalyst)

2.14 g of ammonium metavanadate were dissolved in 500 ml of water having 4 g of oxalic acid dissolved therein. Titanium oxide (anatase type, surface area: 15 m²/g) was suspended in the resulting solution and cesium sulfate and monobasic ammonium phosphate (Example 6) or cesium sulfate and antimony oxide (Example 7) were added thereto, to obtain a suspension. The resulting suspension was sprayed on silicon carbide carriers (100 ml) having a diameter of 3 mm which rotated under heating, followed by calcination at 520° C. As a result, a catalyst containing $V_2O_5$, $TiO_2$, $Cs_2O$ and $P_2O_5$ at a 40:60:0.7:1.0 ratio (Example 6) or containing $V_2O_5$, $TiO_2$, $Cs_2O$ and $Sb_2O_3$ at a 3:97:0.4:2.0 ratio (Example 7) (each weight ratio) was obtained.

(Oxidation Reaction)

The tubular reactor having an internal diameter of 21 mm was filled with 90 g of the catalyst thus obtained and the tube wall temperature was set at the following temperature. A mixture of 4.6 g/hr of 1,1-diphenylethane (having a purity of 85 wt % and containing polyalkylbenzenes as an impurity) and 240 liters of air was then introduced into the reaction tube at SV=3,000 hr⁻¹ (STP). The 1,1-diphenylethane gas concentration at that time was 0.2 vol %.

The total amount of the unreacted raw materials and condensable products discharged from the reaction tube was collected by cooling and then dissolved in a solvent. The results of the analysis of each component by gas chromatography are shown below in Table-2.

TABLE 2

| Example | Composition of catalyst (weight ratio) | Tube-wall temperature (° C.) | Conversion (%) | Selectivity to benzophenone (mole %) |
|---|---|---|---|---|
| | | | Results of Reaction | |
| 6 | V$_2$O$_5$—TiO$_2$—Cs$_2$O—P$_2$O$_5$ 40:60:0.7:1.0 | 350 | 97.8 | 80.7 |
| 7 | V$_2$O$_5$—TiO$_2$—Cs$_2$O—Sb$_2$O$_3$ 3:97:0.4:2.0 | 280 | 99.0 | 81.0 |

EXAMPLES 8 to 18
(Reaction (d))

Reaction was conducted in the same manner as in Example 1 except that the benzophenone obtained in Example 5, 6 or 7 was employed, the catalyst prepared in Example 1 or a catalyst shown in Table 3 below was used, and the reaction conditions were as described in Table 3 below, to obtain a fluorenone (Examples 8 to 17). The results are shown in Table-3.

Further, reaction was conducted under the same conditions as in Example 8 above except 4,4'-dimethylbenzophenone was used as the raw material, to obtain 3,6-dimethylfluorenone (Example 18). The results are also shown in Table-3.

Industrial Utilization Possibility

According to the preparation process of the present invention, fluorenes can be prepared industrially advantageously at high conversion and high selectivity with good productivity using inexpensive raw materials.

By utilizing such a preparation process, fluorenones can be prepared industrially advantageously at high conversion and high selectivity and with good productivity using easily-available diphenylmethanes.

The fluorenones thus obtained are expected to be used as raw materials for heat-resistant epoxy resins, polycarbonates or polyesters.

We claim:
1. A process for the preparation of fluorenes represented by the following formula (II):

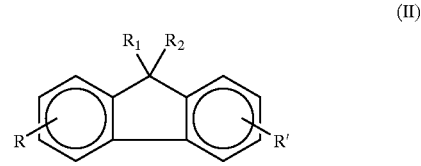

(II)

wherein R$_1$ and R$_2$ each represent a hydrogen atom, a methyl group or an ethyl group or R$_1$ and R$_2$ together represent =O, and R and R' each represent a hydrogen atom, an alkyl group having 1 to 4 carbon atoms or an alkoxy group having 1 to

TABLE 3

| | | (Reaction conditions) | | | (Results of reaction) | |
|---|---|---|---|---|---|---|
| Example | Catalyst | Raw material gas concentration | Sv | Reaction temperature | Conversion of raw material | Selectivity to fluorenone |
| 8 | 5 wt % Pt/activated carbon | 10 mole % | 1000 hr$^{-1}$ | 500° C. | 80.8% | 85% |
| 9 | 5 wt % Pt/Al$_2$O$_3$ | 10 mole % | 1000 hr$^{-1}$ | 500° C. | 61.7% | 73% |
| 10 | 5 wt % Pd/SiO$_2$ | 10 mole % | 1000 hr$^{-1}$ | 400° C. | 49.3% | 61% |
| 11 | Ru/activated carbon ("N2193", produced by Nikki Chemical) | 10 mole % | 1000 hr$^{-1}$ | 450° C. | 50.3% | 65% |
| 12 | MgO (powders formed into a tablet, produced by Wako Pure Chemical) | 10 mole % | 1000 hr$^{-1}$ | 500° C. | 11.9% | 30.3% |
| 13 | ZrO$_2$ (powders formed into a tablet, produced by Wako Pure Chemical) | 10 mole % | 1000 hr$^{-1}$ | 500° C. | 35.0% | 50.5% |
| 14 | Cr$_2$O$_3$—Al$_3$O$_4$ ("N401A", produced by Nikki Chemical) | 10 mole % | 1000 hr$^{-1}$ | 500° C. | 75.0% | 51.0% |
| 15 | Ni—Al$_3$O$_4$ ("N161A", produced by Nikki Chemical) | 10 mole % | 1000 hr$^{-1}$ | 250° C. | 15.0% | 61.0% |
| 16 | Cu—Cr—Zn ("N-211B", produced by Nikki Chemical) | 10 mole % | 1000 hr$^{-1}$ | 250° C. | 20.3% | 74.3% |
| 17 | Fe$_2$O$_3$—K$_2$O ("G-84C", produced by Nissan Girdler Catalyst) | 10 mole % | 1000 hr$^{-1}$ | 500° C. | 62.3% | 64.0% |
| 18 | 5 wt % Pt/activated carbon | 10 mole % | 1000 hr$^{-1}$ | 500° C. | 71.5% | 79% |

4 carbon atoms, which comprises subjecting an aromatic compound represented by the following formula (I):

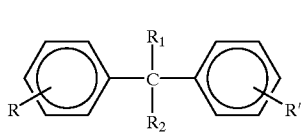
(I)

wherein $R_1$, $R_2$, R and R' are the same as defined above, to a vapor-phase intramolecular cyclodehydrogenation reaction.

2. A process for the preparation of fluorenones represented by the following formula (V):

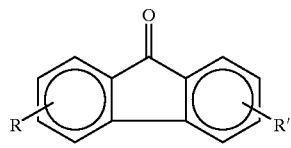
(V)

wherein R and R' each represent a hydrogen atom, an alkyl group having 1 to 4 carbon atoms or an alkoxy group having 1 to 4 carbon atoms, which comprises subjecting diphenylmethanes represented by the following formula (III):

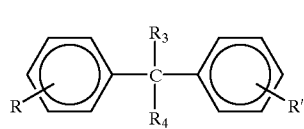
(III)

wherein $R_3$ and $R_4$ each represent a hydrogen atom, a methyl group or an ethyl group, and R and R' are the same as defined above, to a vapor-phase intramolecular cyclodehydrogenation reaction to prepare the corresponding fluorenes represented by the following formula (IV):

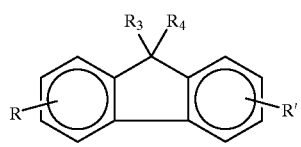
(IV)

wherein $R_3$, $R_4$, R and R' are the same as defined above, and then subjecting the resulting fluorenes to a vapor-phase oxidation reaction.

3. A process for the preparation of fluorenones represented by the following formula (V):

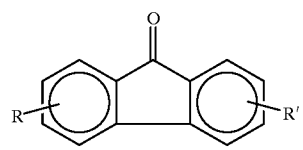
(V)

wherein R and R' each represent a hydrogen atom, an alkyl group having 1 to 4 carbon atoms or an alkoxy group having 1 to 4 carbon atoms, which comprises subjecting diphenylmethanes represented by the following formula (III):

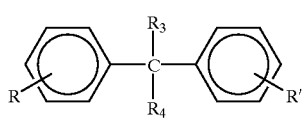
(III)

wherein $R_3$ and $R_4$ each represent a hydrogen atom, a methyl group or an ethyl group and R and R' are the same as defined above, to a vapor-phase oxidation reaction to prepare benzophenones represented by the following formula (VI):

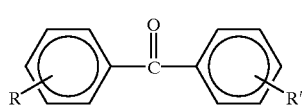
(VI)

wherein R and R' are the same as defined above, and subjecting the resulting benzophenones to a vapor-phase intramolecular cyclodehydrogenation reaction.

4. A process according to any one of claims 1 to 3, wherein the vapor-phase intramolecular cyclodehydrogenation reaction is conducted in the presence of a catalyst.

5. A process according to claim 4, wherein the catalyst contains a noble metal.

6. A process according to claim 4, wherein the catalyst is a platinum supported catalyst.

* * * * *